United States Patent [19]

Williamson et al.

[11] Patent Number: 5,246,970
[45] Date of Patent: Sep. 21, 1993

[54] METHOD OF INHIBITING NITRIC OXIDE FORMATION

[75] Inventors: Joseph R. Williamson, Town and Country; John A. Corbett, St. Louis; Michael L. McDaniel, Glendale; Ronald G. Tilton, St. Louis, all of Mo.

[73] Assignee: Washington University, St. Louis, Mo.

[21] Appl. No.: 906,632

[22] Filed: Jun. 30, 1992

Related U.S. Application Data

[63] Continuation-in-part of Ser. No. 807,912, Dec. 16, 1991, abandoned.

[51] Int. Cl.⁵ ............................................. A61K 31/155
[52] U.S. Cl. ..................................... 514/632; 514/903
[58] Field of Search ................................. 514/632, 903

[56] References Cited

U.S. PATENT DOCUMENTS 4,758,583  7/1988  Cerami et al. .................... 514/399
4,983,604  1/1991  Ulrich et al. .................... 514/238.5
5,128,360  7/1992  Cerami et al. .................... 514/634

FOREIGN PATENT DOCUMENTS 450598 10/1991 European Pat. Off. .

OTHER PUBLICATIONS

Bredt et al., Nature 351, 714-718 (1991).
Moncada et al., Pharmacol. Rev. 43, 109-142 (1991).
Brownlee et al., Science 232, 1629-1632 (1986).
Bucala et al., J. Clin. Invest. 87, 432-438 (1991).
Tilton et al., Invest. Ophthalmol. Vis. Sci. 31, 342 (1990).
Williamson et al., Diabetes & Metabolisme 16, 369-370 (1990).
Chang et al., Diabetes 40 (Supp. 1) 210A (1991).
Corbett et al., J. Biol. Chem. 266, 21351-21354 (1991).
Chem. Absts. 115:248104, Griffith WO 91 04,023 (1991).

Primary Examiner—Frederick E. Waddell
Assistant Examiner—Raymond J. Henley, III
Attorney, Agent, or Firm—Scott J. Meyer

[57] ABSTRACT

A method is disclosed for inhibiting nitric oxide formation in a warm blooded mammal which comprises administering to said mammal an effective nitric oxide inhibitory amount of aminoguanidine.

5 Claims, 6 Drawing Sheets

METHOD OF INHIBITING NITRIC OXIDE FORMATION

ACKNOWLEDGEMENT OF GOVERNMENT SUPPORT

This work was supported in part by National Institutes of Health grants KD06181, T32 DK07296, EY06600, HL39934, KD20579, NS27321 and DK39934.

CROSS-REFERENCE TO RELATED APPLICATION

This is a continuation-in-part of application Ser. No. 07/807,912, filed December 16, 1991 now abandoned.

BACKGROUND OF THE INVENTION

This invention relates to a method of inhibiting nitric oxide formation in warm blooded mammals and, more particularly, to the administration of aminoguanidine as an inhibitor of nitric oxide production.

Nitric oxide synthase catalyzes the mixed functional oxidation of L-arginine to L-citrulline and nitric oxide (NO·1,2). NO· appears to function as either a signaling or an effector molecule depending on the isoform of the enzyme. The constitutive isoform of nitric oxide synthase produces small amounts of NO· which activate guanylate cyclase resulting in the formation of cGMP which mediates endothelium-dependent relaxation (2) and neural transmission (3). NO· is produced in much larger amounts by the cytokine and endotoxin inducible isoform of nitric oxide synthase, and in macrophages functions as an effector molecule which appears to mediate the cytotoxic actions of macrophages on target cells (4). Since NO· is a potent vasodilator and increases blood flow, and since vasoactive agents (such as histamine and bradykinin), which stimulate NO· production increase both blood flow and vascular permeability, NO· may be a candidate for mediating increases in blood flow and vascular permeability induced by diabetes and elevated glucose (5).

Recently, Interleukin-1 (IL-1) has been shown to induce the expression of the cytokine inducible isoform of nitric oxide synthase in pancreatic islets. The production of NO· has been proposed to be the effector molecule which mediates IL-1's inhibitory affects on islet function (6,7). Generation of an IL-1-induced EPR detectable iron-nitrosyl complex, which is prevented by $N^G$-monomethyl-L-arginine (NMMA), has been used to confirm the formation of nitric oxide by islets (8). Also, the protein synthesis inhibitor, cycloheximide has been shown to block IL-1-induced nitrite formation, cGMP accumulation, and EPR detectable iron-nitrosyl complex formation by islets, thus establishing that IL-1 induces the cytokine inducible isoform of nitric oxide synthase in pancreatic islets (7).

The pathogenesis of diabetic complications has been linked to imbalances in sorbitol, myo-inositol, and 1,2-diacyl-sn-glycerol metabolism, and to non-enzymatic glycation of cellular and extracellular constituents (5). The glycation link is supported by evidence that aminoguanidine, a nucleophilic hydrazine compound, interferes with the formation of these glycation products and also attenuates the development of several diabetes-induced vascular (5,9), neural (10), and collagen changes (11). Bucala et al. (12) recently reported that quenching of NO· in vitro by glycated albumin is attenuated by aminoguanidine (present during exposure of albumin to glycating agents) and suggested that glycation products may impair endothelium-dependent relaxation by attenuating NO· activity.

BRIEF DESCRIPTION OF THE INVENTION

In accordance with the present invention a novel method of inhibiting nitric oxide formation in warm blooded mammals is provided. The method comprises administering to a warm blooded mammal a small but effective amount of aminoguanidine to inhibit nitric oxide production.

At the present time the pathogenesis of diabetic complications remains obscure and there is no known medication which has been shown to prevent them. Although diabetic complications are strongly linked to severity of diabetes as reflected by blood sugar levels and glycated hemoglobin, the efficacy of attempts to prevent and/or reverse diabetic complications by efforts to normalize blood sugar levels remains to be documented.

Although there is a considerable body of evidence linking diabetic complications in experimental animals to increased metabolism of glucose via the sorbitol pathway, it remains unclear whether inhibitors of this metabolic pathway will be efficacious in preventing complications in human diabetics. Aminoguanidine does not appear to affect sorbitol pathway metabolism, since tissue levels of sorbitol in diabetic rats are unaffected by aminoguanidine.

While aminoguanidine has been reported to prevent formation of advanced nonenzymatic glycation products, the mechanism that mediates this effect remains unclear. Nonenzymatic glycation products have been observed in a large number of cellular and extracellular constituents and in tissues of nondiabetic as well as in diabetic humans and animals. These products appear to form and accumulate nonselectively in virtually all tissues whether or not they are sites of clinically significant complications of diabetes. Thus the importance of advanced glycation endproducts in the pathogenesis of diabetic complications remains unclear.

The vascular functional abnormalities prevented by aminoguanidine are a characteristic feature of diabetic complications and are closely linked (and may contribute) to the end-stage structural changes associated with organ failure.

A novel feature of aminoguanidine is that it selectively prevents the development of vascular dysfunction in ocular tissues, nerve, and aorta of diabetic rats (but does not lower blood glucose levels) without affecting vascular function in those tissues in which vascular function is unaltered by diabetes. Similarly, aminoguanidine (at the same dose given to diabetics) has no effect on vascular function in any tissues of control rats, including those in which it prevents vascular dysfunction in diabetics.

A second remarkable and unexpected feature of aminoguanidine is that while it is equipotent to NMMA (an established inhibitor of both the inducible and constitutive isoforms of nitric oxide synthase) in its ability to inhibit IL-1β induced nitric oxide synthase in cultured Rin m5F cells (a rodent insulinoma cell line), it is only ~1/40th as potent as NMMA in elevating arterial blood pressure. This can provide a great therapeutic advantage for aminoguanidine since it can enable administration of the drug in doses which inhibit induced nitric oxide synthase in the vasculature and in other tissues affected by disease processes without inhibiting constitutive vascular nitric oxide synthase (which would cause hypertension).

The present discovery of the useful inhibitory activity of aminoguanidine against nitric oxide production suggests further uses of this agent for:

1. Prevention of diabetic complications (based on evidence that aminoguanidine prevents diabetes-induced vascular dysfunction).

2. Prevention/treatment of a broad spectrum of acute and chronic diseases which may be linked to production of nitric oxide by activated macrophages and other cells. Examples of such diseases include type 1 diabetes, arthritis, neuritis, neurological disorders such as multiple sclerosis, myocardial infarcts, strokes, glomerulonephritis, collagen diseases, rejection of transplanted organs, and other diseases mediated by immune mechanisms.

3. Treatment of hypotension, i.e., septic shock.

4. Development of analogues of aminoguanidine for inhibiting production of nitric oxide.

5. Development of analogues of aminoguanidine which can serve as substrate for production of nitric oxide and thus may be useful for prevention/treatment of hypertension, coronary artery disease, peripheral vascular disease, vasospasm, and occlusive vascular disease in general.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention taken in conjunction with the accompanying drawings in which briefly:

Figure 1A:
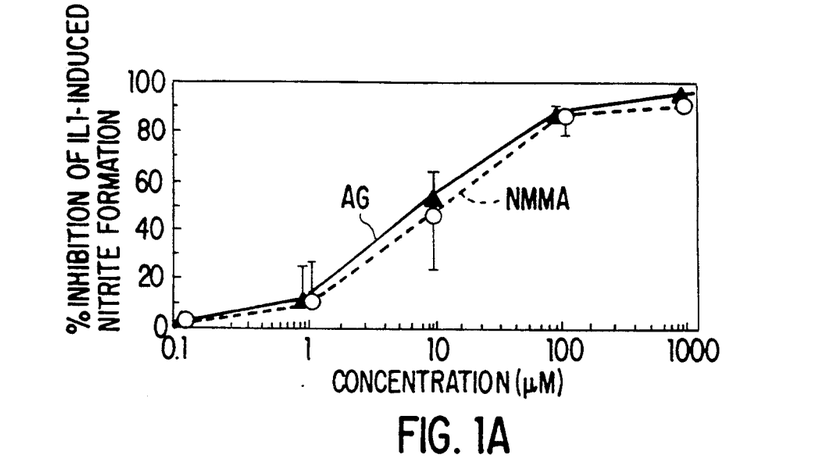
FIG. 1 is a graphical representation which shows in Panel A, the effects of aminoguanidine (AG) on IL-1$\beta$-induced nitrite formation; Panel B, cGMP accumulation by Rin m5F cells; and Panel C, IL-1$\beta$-induced inhibition of glucose stimulated secretion by islets.

Since aminoguanidine contains strong structural similarities to L-arginine and the competitive inhibitor of nitric oxide synthase, viz. NMMA, in that these compounds contain two chemically equivalent guanidino nitrogen groups, the effects of aminoguanidine on IL-1$\beta$-induced formation of nitrite, and cGMP by Rin m5F cells were examined and compared to the effects of NMMA in similar tests. The Rin m5F cell line is an insulinoma cell line of the rodent $\beta$-cell that has recently been shown to contain the cytokine-inducible isoform of nitric oxide synthase (13). FIG. 1A demonstrates the dose response of aminoguanidine and NMMA on IL-1$\beta$-induced formation of nitrite (an oxidation for 18 hrs with 5 units/ml IL-1$\beta$ ±the indicated concentrations of aminoguanidine or NMMA. Both compounds inhibit IL-1$\beta$-induced nitrite production in a dose dependent fashion, in which both compounds inhibit half maximally at a concentration of ~10 $\mu$M.

Figure 1B:
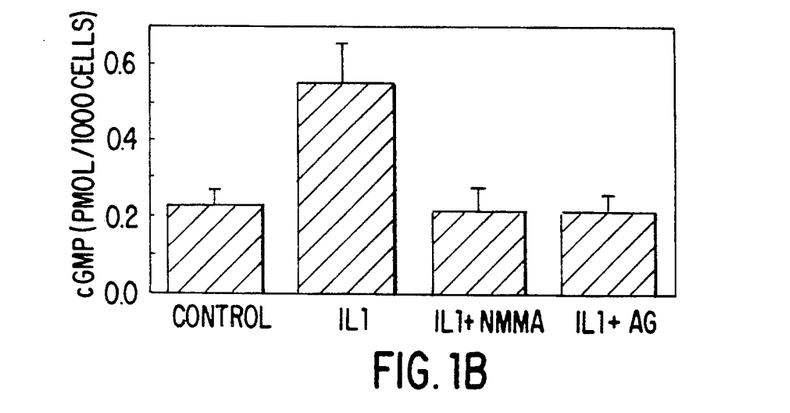

Next, the effects of aminoguanidine on IL-1$\beta$-induced cGMP accumulation, a very sensitive measure of NO production (7), were examined. Rin m5F cells were treated for 18 hrs with 5 units/ml IL-1$\beta$±0.5 mM NMMA, or ±0.5 mM aminoguanidine, followed by a 3 hr incubation with the phosphodiesterase inhibitor isobutyl-methylxanthine (1 mM). FIG. 1B demonstrates that IL-1$\beta$-induced accumulation of cGMP in Rin m5F cells was completely blocked by aminoguanidine and by NMMA, providing further evidence that aminoguanidine inhibits nitric oxide synthase.

Figure 1C:
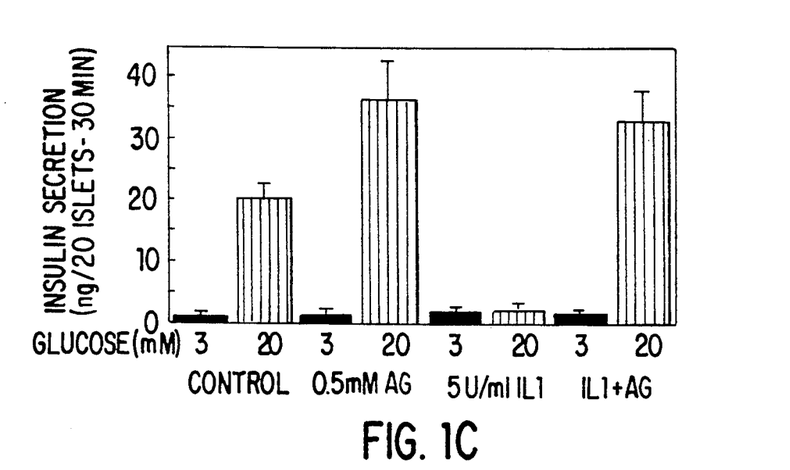

The effect of aminoguanidine on IL-1$\beta$-induced inhibition of glucose-stimulated insulin secretion was also examined. FIG. 1C demonstrates that glucose-stimulated insulin secretion is significantly inhibited by pretreatment of islets for 18 hrs with IL-1$\beta$. Aminoguanidine (0.5 mM) completely prevents this IL-1$\beta$-induced inhibition of insulin secretion. Aminoguanidine in the absence of IL-1$\beta$ slightly potentiates insulin secretion by islets, although this effect is not statistically significant (p>0.075) when compared to insulin secretion by the untreated control islets. NMMA also has been shown to slightly potentiate insulin secretion and completely block IL-1$\beta$ induced inhibition of insulin secretion (8). The slight stimulation of insulin secretion induced by NMMA and aminoguanidine may be due to the inhibition of both the constitutive and inducible isoforms of nitric oxide synthase (7,8).

Figure 2:
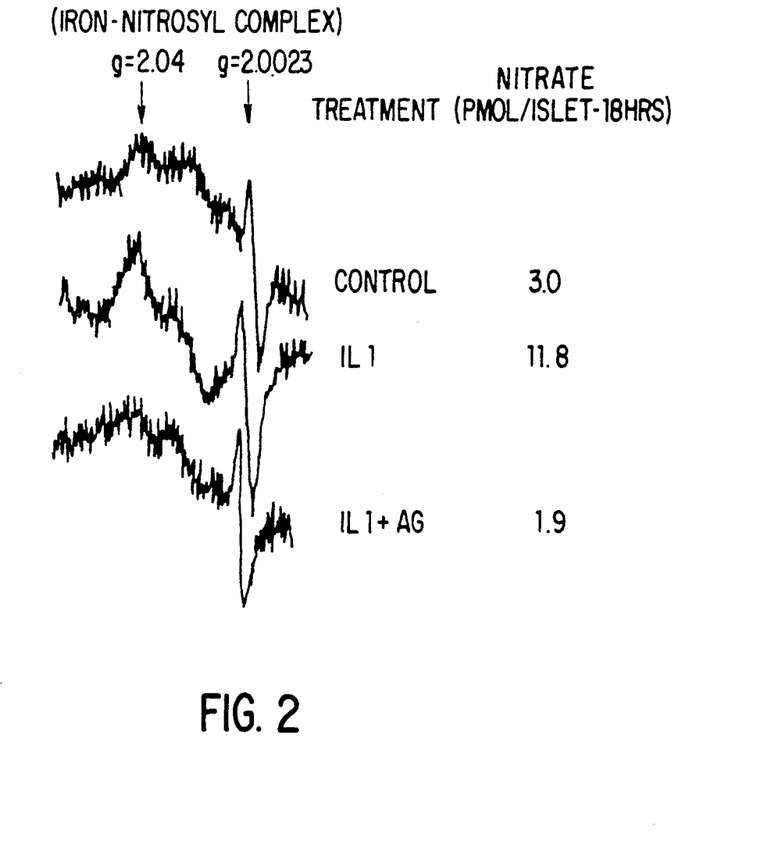
FIG. 2 shows by EPR spectroscopy the effects of aminoguanidine on IL-1-induced iron-nitrosyl complex formation by islets.

To confirm that aminoguanidine inhibits IL-1$\beta$-induced nitric oxide synthase activity, the effects of aminoguanidine on IL-1$\beta$-induced formation of a g=2.04 EPR-detectable iron-nitrosyl feature by islets was investigated. FIG. 2 demonstrates that aminoguanidine (0.5 mM) completely prevents the formation of this IL-1$\beta$ induced iron-nitrosyl feature. Also shown in this figure is the concurrent formation of nitrite by the same islets used for EPR spectroscopy. The formation of this g=2.04 iron-nitrosyl EPR-detectable feature has been used previously to confirm the formation of NO in islets treated with IL-1$\beta$ (7,8), in activated macrophages (14), and in target cells recognized by activated macrophages (15). The formation of this feature (an iron-dinitrosyl complex) is consistent with the possibility that removal of non-heme iron from iron containing enzymes may be the mechanism by which nitric oxide inhibits insulin secretion (7,14,15). These results confirm that aminoguanidine is a potent inhibitor of the cytokine-inducible isoform of nitric oxide synthase.

Figure 3:
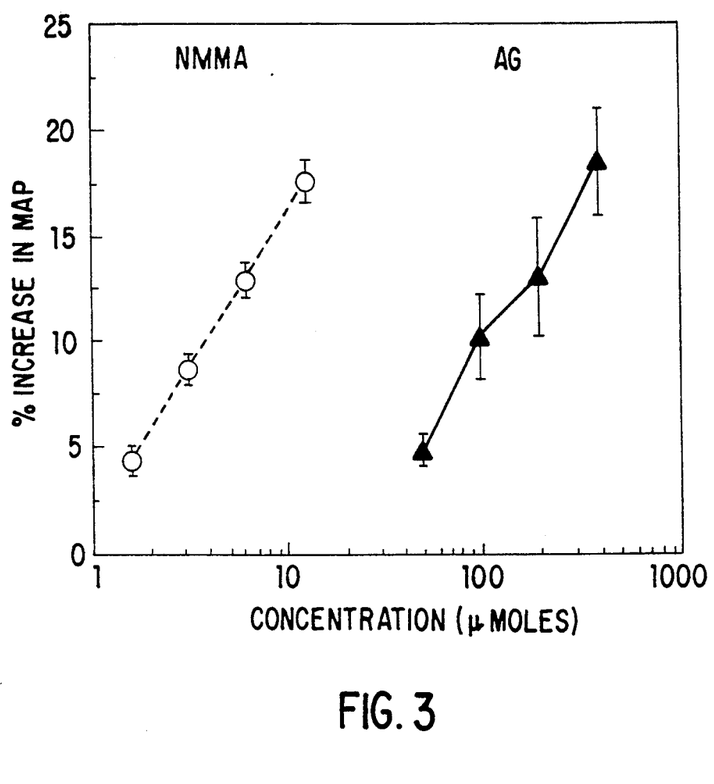
FIG. 3 is a graphical representation which shows the effects of aminoguanidine (AG) and $N^G$-monomethyl-L-arginine (NMMA) on mean arterial blood pressure (MAP).

Effects of aminoguanidine on constitutive (vascular) nitric oxide synthase activity were assessed by monitoring mean arterial blood pressure (MAP) changes following intravenous injection of aminoguanidine in anesthetized, normal rats. The dose responses of aminoguanidine and NMMA are shown in FIG. 3. Both compounds increase MAP in a dose-dependent fashion, although NMMA is at least 10 fold more potent than aminoguanidine. The difference in sensitivity does not appear to be due to the inhibitory effects of aminoguanidine on diamine oxidase activity (16), since pretreatment with diphenhydramine (an $H_1$ receptor blocker) has no effect on aminoguanidine-induced increases in MAP (13). These observations suggest that while aminoguanidine and NMMA are equipotent inhibitors of cytokine-induced nitric oxide synthase in vitro. aminoguanidine unexpectedly and advantageously is much less potent than NMMA as an inhibitor of the constitutive isoform of nitric oxide synthase in vivo.

Figure 4A:
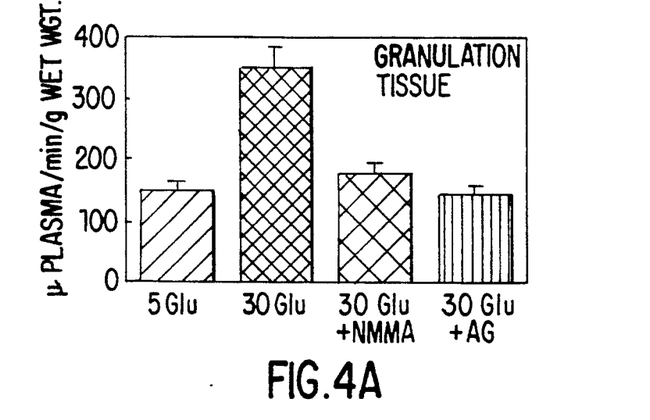
FIG. 4 is a graphical representation which shows the effects of aminoguanidine (AG) and $N^G$-monomethyl-L-arginine (NMMA) on glucose-(Glu) in Panel A, and diabetes-induced increases in vascular albumin permeation in Panel B and blood flow in Panel C.

To assess the putative role of NO· in mediating glucose-induced vascular dysfunction, the effects of 1 mM aminoguanidine or 1 mM NMMA on 30 mM glucose-induced increases in vascular clearance of $^{131}I$-albumin were examined in a skin chamber, granulation-tissue model in nondiabetic rats (17). As shown in FIG. 4A, exposure of newly forming granulation tissue vessels to 30 mM glucose twice daily for 6–7 days caused a ~2 fold (P <0.005) increase in $^{131}I$-albumin clearance, which is completely prevented by coadministration of aminoguanidine or NMMA. Similarly, in rats with streptozotocin-induced diabetes of 5 weeks duration, aminoguanidine (50 mg/kg/day injected sc) prevents the 2–4 fold increases in $^{131}I$-albumin clearance in ocular tissues (P<0.001) including the retina (FIG. 4B), sciatic nerve (9), and aorta (13). Likewise, in rats with diabetes of 4 months duration, aminoguanidine prevented blood flow increases (P<0.001) in the retina (FIG. 4C), as well as other ocular tissues and sciatic nerve (13). In these tests aminoguanidine had no effect on blood pressure or on tissue sorbitol and myo-inositol levels (13).

The finding that aminoguanidine and NMMA prevent diabetes- and glucose-induced increases in $^{131}I$-albumin permeation implies a role for NO· in mediating impaired vascular barrier function as well as increased blood flow in diabetes. This interpretation is consistent with evidence that: 1) increased vascular permeability and blood flow induced by vasoactive agents such as histamine and bradykinin in dondiabetic animals are coupled to increased NO· production, and 2) NO· modulates the metabolism and function of the cells in which it is produced (2,4).

The likelihood that normalization of vascular function in these tests reflects inhibition of nitric oxide synthase activity by aminoguanidine rather than prevention of advanced glycation end products is strongly supported by the brief duration (48 hour maximum) of elevated glucose in the granulation tissue model (17), and the prevention by aminoguanidine of 1 mM sorbitol-induced increased vascular albumin permeability in granulation tissue in nondiabetic rats (18). These findings, coupled with evidence that pyruvate and inhibitors of the sorbitol pathway also prevent glucose-induced increased vascular permeability (17,18), suggest that interactions between sorbitol pathway-linked redox imbalances in AND(P)AND(P)H⁺ (5), NADPH dependent nitric oxide synthesis, and inhibition of oxidative metabolism by NO· (4) may be important in the pathogenesis of diabetic complications.

The effects of aminoguanidine were also assessed in experimental allergic encephalomyelitis (EAE) induced in rats by intravenous injection of activated, myelin basic protein specific CD8+ T cells.

Experimental allergic encephalomyelitis (EAE) is a transient, paralytic central nervous system (CNS) autoimmune inflammation that is often employed as a model of the human disease multiple sclerosis. The effector cells are $T_H1$, CD4+, CD25+, CD45R− lymphocytes which are specific for a myelin antigen, usually myelin basic protein (23). The inflammation which occurs in the CNS following an intravenous injection of these lymphocytes is composed chiefly of CF4+ lymphocytes and macrophages (24). Over the past decade there has been extensive progress made in dissecting the cellular and molecular participants operating in the production of EAE. Monoclonal antibodies directed against T-lymphocytes (25) and macrophages (26) prevent or interrupt EAE development. Studies have implicated specific cytokines in the pathogenesis of EAE (27). In addition, a number of substances have been shown to inhibit or ameliorate the condition (28). In aggregate, these investigations have provided evidence that macrophages, T-cells, and their secreted products play a central role in the pathogenesis of EAE. Identification of the specific mediators in EAE may offer possibilities for therapeutic intervention in human T-cell mediated autoimmune disease. As shown herein in FIG. 5 and Table 1, the maximum clinical severity of EAE and the duraton of illness were significantly inhibited by twice daily subcutaneous injection of 100 mg/kg body weight aminoguanidine in rats. Moreover, histological staining for neuronal NADPH diaphorase, a NO synthase, revealed that the spinal cord of rats with EAE was positive in both parenchymal blood vessel walls and in anterior horn cell neurons. Normal rats and rats with EAE inflammation treated with aminoguanidine showed only the neuronal positivity. These results suggest that: 1) nitric oxide is a secreted product of the inflammatory cells present in the inflamed regions of the central nervous system in EAE, 2) increased nitric oxide production plays a role in the pathogenesis of the EAE clinical symptoms, and 3) NO synthase inhibitors may have therapeutic potential for the treatment of multiple sclerosis in humans.

In order to further illustrate the invention, the following detailed examples were carried out although it should be understood that the invention is not limited to these specific examples or the details described therein. The results obtained in these examples are shown in the accompanying FIGS. 1 to 4.

EXAMPLE 1

This example illustrates the effects of aminoguanidine on IL-1β-induced nitrite formation, and cGMP accumulation by Rin m5F cells, and IL-1β-induced inhibition of glucose stimulated insulin secretion by islets. (FIG. 1A). Rin m5F cells, obtained from the Washington University Tissue Culture Support Center, were removed from growth flasks (55–80 million cells/flask) by trypsin/EDTA treatment, and aliquoted into 1 ml Petri dishes (1–2 million Rin m5F cells per condition). Cells were incubated for 18 hrs (under an atmosphere of 95% air and 5% $CO_2$) in 1 ml of complete CMRL-1066 tissue culture media (CMRL supplemented with 10% heat-inactivated, fetal bovine serum, 2 mM L-glutamine, 50 units/ml penicillin, and 50 μg/ml streptomycin), or complete CMRL-1066 supplemented with aminoguanidine or NMMA. Following incubation, the supernatant was removed and nitrite was determined on 100 μl aliquots by conventional procedures as previously described (8, 19). Results are expressed as a mean±SEM of data from at least 3 independent tests. (FIG. 1B). cGMP accumulation was determined on 8 million Rin m5F cells incubated for 18 hrs in 1 ml of complete CMRL-1066 supplemented with 5 units/ml IL-1β, 0.5 mM aminoguanidine-HCl, 0.5 mM NMMA, or both IL-1β and aminoguanidine-HCl or IL-1β and NNMA as described above. Following the 18 hr treatment the Rin m5F cells were incubated an additional 3 hrs in 1 ml of complete CMRL-1066 containing 1 mM isobutyl-methylxanthine. cGMP formation induced by IL-1β was measured using a conventional cGMP RIA kit commercially available from NEN-DuPont (7). Data is expressed as the mean ±SEM of 3 independent tests. (FIG. 1C). For insulin secretion studies islets were isolated by collagenase digestion from male Sprague-Dawley rats (250–300 g) by conventional procedures as described previously (20). The isolated islets (120/ml) were pretreated in complete CMRL-1066, or complete CMRL-1066 containing 5 units/ml IL-1β, 0.5 mM aminoguanidine-HCl, or IL-1β and aminoguanidine-HCl for 18 hrs at 37° C. under an atmosphere of 95% air and 5% $CO_2$. Following pretreatment the islets were washed 3 times in 1 ml/wash of Krebs-Ringer bicarbonate buffer (KRB: 25 mM Hepes, 115 mM NaCl, 24 mM $NaHCO_3$, 5 mM KCl, 1 mM $MgCl_2$, 2.5 mM $CaCl_2$, pH 7.4) containing 3 mM D-glucose, and 0.5% BSA. Groups of 20 islets were counted into 10×75 mm siliconized borosilicate tubes and preincubated for 30 min in 200 μl of the same buffer. The preincubation buffer was removed and glucose-stimulated insulin secretion was initiated by the addition of 200 μl of fresh KRB containing 3 mM D-glucose or 20 mM D-glucose followed by an incubation of 30 min. Both the preincubation and incubation were performed under an atmosphere of 95% air and 5% $CO_2$ at 37° C. Insulin content of the incubation media was measured by radioimmunoassay. Results are expressed as the mean±SEM of data from three individual tests. Statistical significance (P<0.05) was determined by the Students t-test.

EXAMPLE 2

This example illustrates the effects of aminoguanidine on IL-1-induced iron-nitrosyl complex formation by islets. Isolated islets (2400) were cultured in 3 ml of complete CMRL-1066, or complete CMRL-1066 containing 5 units/ml IL-1β, 0.5 mM aminoguanidine-HCl, or both IL-1β and aminoguanidine-HCL for 18 hrs at 37° C. under an atmosphere of 95% air and 5% $CO_2$. The islets were isolated by centrifugation and frozen at −70° C. EPR spectroscopy was performed at 77 K on the islets using a Varian E-109 spectrometer equipped with a 9.5 GHz microwave bridge. The power was 1 mW, the modulation frequency was 100 kHz, the modulation amplitude was 8 guass, and the microwave frequency was 9.109 GHz. Nitrite was determined as described in Example 1 (FIG. 1A) on 100 μl aliquots of the same islet culture supernatant used for EPR spectroscopy. The data shown in FIG. 2 are representative of 3 individual tests containing at least 2400 islets per condition. The IL-1β-induced iron-nitrosyl g=2.04 complex and the delocalized electron g=2.002 features (found in all cells) are indicated by arrows.

EXAMPLE 3

This example illustrates the effects of aminoguanidine and NMMA on mean arterial blood pressure. Normal male, Sprague-Dawley rats were anesthetized with 100 mg/kg body weight Inactin, the left femoral vein (for tracer injection) and right iliac artery (for monitoring blood pressure) were cannulated with polyethylene tubing filled with heparinized saline, and the trachea was cannulated and connected to a small rodent respirator for continuous ventilatory support. Following stabilization of arterial pressure, increasing amounts of aminoguanidine or NMMA were injected intravenously in separate animals and the peak pressure increase was recorded. Results are shown in FIG. 3 and are expressed as a percent increase in pressure above baseline and represent a mean ±SEM. n=6 for aminoguanidine and n=5 for NMMA.

EXAMPLE 4

Figure 4B:
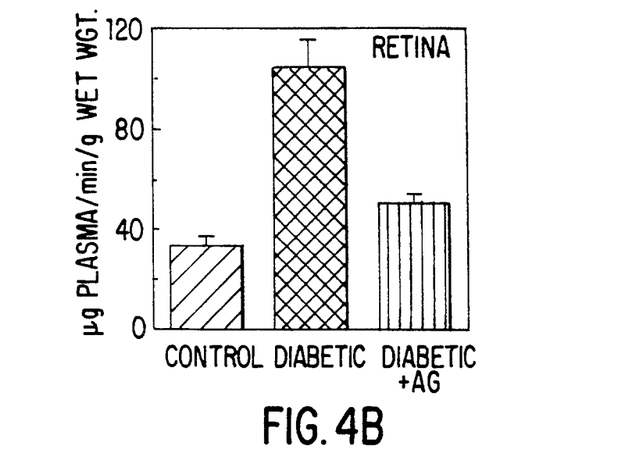
Figure 4C:
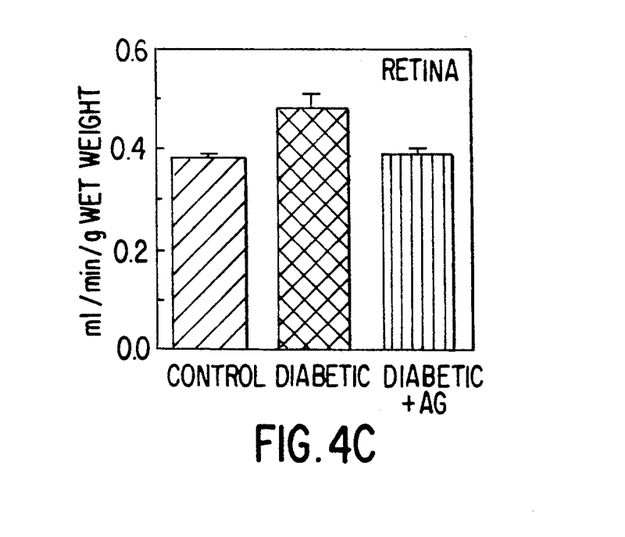

This example illustrates the effects of aminoguanidine and NMMA on glucose- and diabetes-induced increases in vascular albumin permeation and blood flow. (FIG. 4A). Glucose-induced increases in vascular albumin permeation were assessed in a conventional granulation tissue, skin-chamber model (17). Briefly, 2-cm circles of skin were removed from the back on either side of the midline of anesthetized, normal nondiabetic rats. A plastic chamber equipped with stainless steel screwcaps (which can be readily removed to permit addition of pharmacological agents to the new granulation tissue vessels as they form inside the chamber) is sutured to the skin at the margins of the wound. Seven days after inserting the chambers, 1.5 ml of Hepes buffer, pH 7.4 (25 mM Hepes, 137 mM NaCl, 4.2 mM KCl, 3 mM $Na_2HPO_4$, 0.3 mM L-arginine, 100 μg/ml penicillin G, 10 μg/ml gentamicin) containing 5 mM glucose, or 30 mM glucose, or 30 mM glucose+1 mM aminoguanidine, or 30 mM glucose+1 mM NMMA were added to each individual chamber (n=4 for each test condition). Solutions were prepared fresh daily and were added twice daily to each chamber (9:00 AM and 5:00 PM) for 7 days. Within an hour of the last treatment, albumin clearance was assessed by conventional procedures as previously described (21). (FIG. 4B). Male, Sprague-Dawley rats initially weighing ∼250 g were divided into nondiabetic controls (n=8), controls treated with 50 mg/kg body weight aminoguanidine (n=8), untreated diabetics (n=11), and diabetics treated With the same dose of aminoguanidine (n=9). Diabetes was induced by i.v. injection of streptozotocin, at which time, rats in groups 2 and 4 were given aminoguanidine subcutaneously once daily. Rats were used for vascular permeability studies after 5 weeks of diabetes. Albumin permeation of retinal vessels was assessed by a conventional quantitative isotope-dilution technique described previously (21) based on the injection of $^{131}$I-BSA (circulation time 10 min) for assessment of vascular albumin permeation and $^{125}$I-BSA (circulation time 2 min) as a vascular space reference tracer to correct intravascular $^{131}$I-BSA tissue activity. calculate $^{131}$I-BSA vascular clearance (μg plasma/g wet weight/min), $^{131}$I-BSA activity in the retina was corrected for tracer contained within retinal vessels; the vascular-corrected $^{131}$I-BSA retina activity was divided by a time-averaged $^{131}$I-BSA plasma activity obtained from the plasma samples taken at 1, 5, and 10 min after tracer injection, then by the tracer circulation time (10 min) and normalized per g tissue wet weight. (FIG. 4C). Regional blood flows (n=7 for each group) were measured after 4 months of diabetes using $^{85}$Sr-labeled microspheres by conventional techniques as described previously (22). To calculate regional blood flows, the total activity of $^{85}$Sr in the retina was divided by the total activity of $^{85}$Sr in the reference blood sample obtained from the withdrawal syringe, then multiplied by the pump withdrawal rate, and expressed as ml/g tissue wet weight per minute.

Example 5

Figure 5:
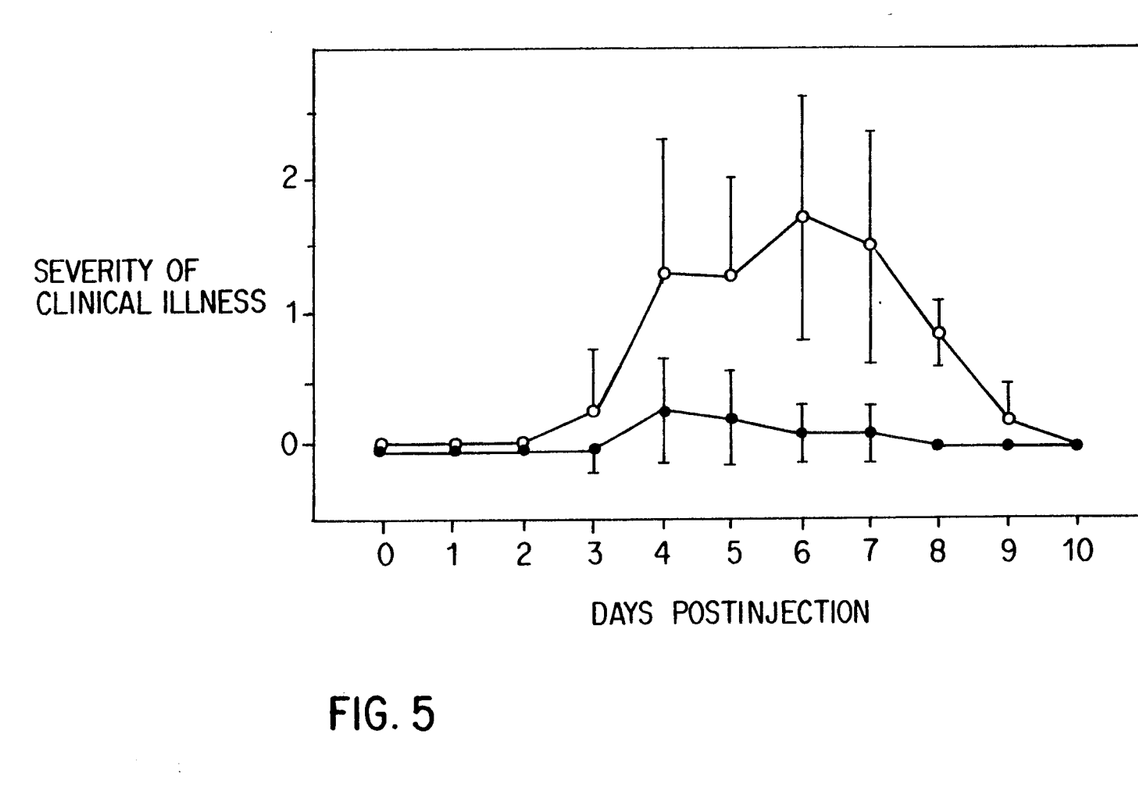
FIG. 5 is a graphical representation of experimental allergic encephalomyelitis (EAE) induced in rats by intravenous injection of activated, myelin basic protein specific CD8+ T cells which shows the average daily progression of clinical illness for all control (open circles) and aminoguanidine treated (filled circles) rats.

This example illustrates the effects of aminoguanidine on experimental-allergic encephalomyelitis (EAE), induced in rats by intravenous injection of activated, myelin basic protein specific CD8+ T cells, which is a transient, paralytic, central nervous system autoimmune inflammation model of multiple sclerosis. The test protocols and results shown in FIGS. 5 and 6 were as follows:

FIG. 5, Effects of daily subcutaneous injection of aminoquanidine on clinical severity of experimental allergic encephalomyelitis in rats. EAE was induced by the injection of $T_H$ lymphocytes, selected for guinea pig myelin basic protein reactivity and stimulated for 3 days with antigen in the presence of accessory cells by conventional procedure as previously described (23) into male Lewis rats 2 to 3 months of age (Charles River Laboratories, Wilmington, Mass.). Rats were housed (three to four per cage) and cared for in accordance with the guidelines of the University Committee for the Humane Care of Laboratory Animals and in accordance with NIH guidelines on laboratory animal welfare. Rats were allowed standard rat chow (Ralson Purina, Richmond, Ind.) and water ad libitum, and were on a 12 hour light/dark cycle. Aminoguanidine hemisulfate (100 mg/kg body weight) was injected subcutaneously twice daily (0900 and 1500 hr) in a double blind fashion starting 24 hours prior to the injection of antigen-activated lymphocytes. Clinical illness was scored twice daily for all rats as: 0 if the rat had no paralysis; 1+ if the rat had a flaccid tail; 2+ if the hindlimbs were paralyzed; and 3+ if in addition to paralysis the animal exhibited a moridbund state by not moving to stimuli.

Figure 6A:
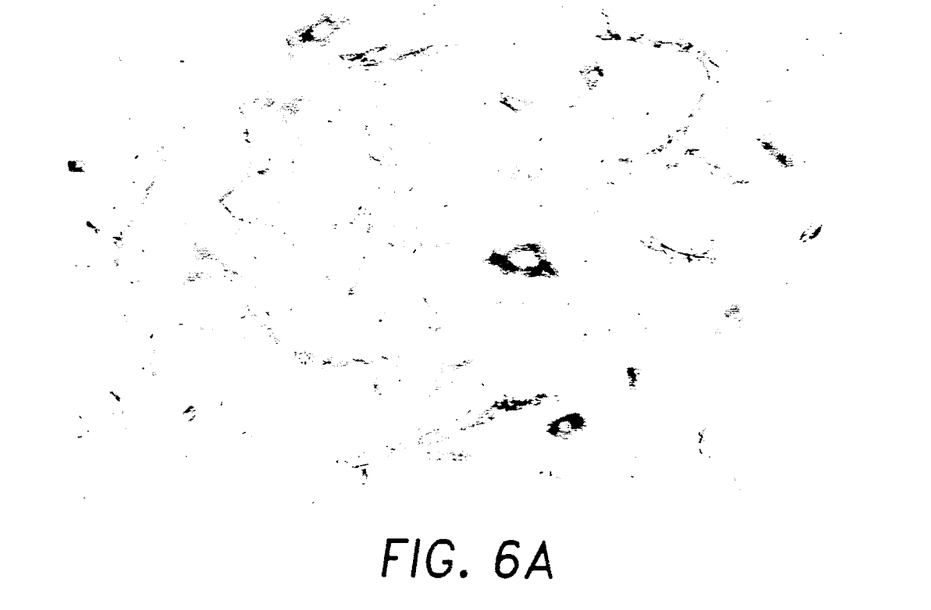
FIG. 6 shows in two parts, FIG. 6A and FIG. 6B, histological sections of the spinal cord from rats examined for inflammation and the presence and distribution or NADPH diaphorase in which A., a section from a rat paralyzed with EAE as in FIG. 5, is compared with B., a comparable section from a matched rat which had been treated with aminoguanidine.
Figure 6B:
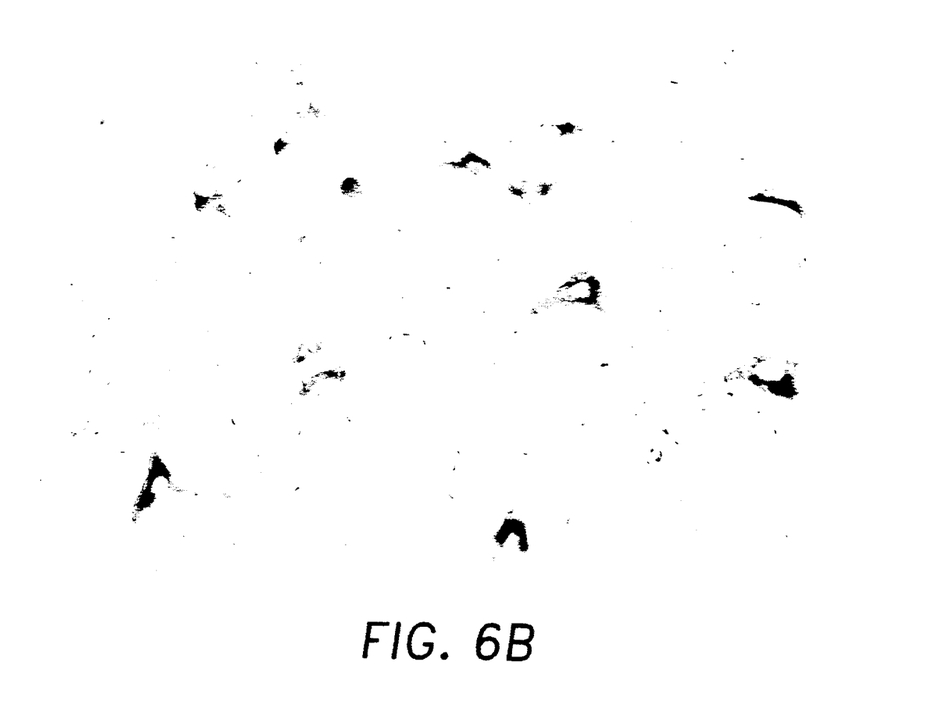

FIG. 6. Histological sections of the anterior horn area of rat spinal cord stained for NADPH diaphorase using nitro-blue-tetrazoleum as a chromogen (x325). Under deep anesthesia, rats were perfused via the aorta with a phosphate-buffered saline rinse followed by 100 ml 2% paraformaldehyde solution in 0.1 M phosphate buffer, pH 7.4. The spinal cord was removed, cut into 3-4 mm thick blocks, fixed for an additional 1-2 hours, rinsed using 0.2 M phosphate buffer, pH 7.4, and equilibrated in 30% sucrose in water overnight. 8 μm thick cryostat sections were stained for NADPH diaphorase. FIG. 6A, shows a section from a rat paralyzed with EAE which demonstrates enzyme activity in both anterior horn neurons and diffusely in the walls of parencymal blood vessels. FIG. 6B shows a comparable section from a matched rat which had been treated with aminoguanidine which had CNS inflammation but exhibited no illness. In this section only the anterior horn neurons are positive.

RESULTS

FIG. 5 shows the average daily progression of clinical illness for all control and aminoguanidinetreated rats, and it can be seen that the aminoguanidine-treated rats developed paralysis later, the severity was less, and recovery was more rapid than in the untreated control group. These results are quantified in Table 1. In control rats in which the paralysis was allowed to complete its clinical course (eight animals in each group were killed at peak illness), the average duration of illness was ~5 days, the maximum clinical severity reached 2.2, and the overall illness score (sick days times number of days at maximum illness) was 11.3. Significant reductions in duration of illness, maximum clinical severity, and overall illness score (p<0.001) were observed in rats treated twice daily with 100 mg/kg body weight aminoguanidine injected subcutaneously. The average weight loss was ~13% for control and ~9% for aminoguanidine-treated rats. The histologic grade was 2.6±0.7 and 2.3±0.6 for controls and aminoguanidine-treated rats, respectively. It is noteworthy that the dramatic effect of aminoguanidine on the clinical signs of EAE was not paralleled by a corresponding decrease in inflammation. It is believed that this discrepancy may arise from the ability of aminoguanidine to inhibit the release of pathogenic substances by the cellular participants in the inflammation without decreasing the prevalence of the inflammatory cells in the target organ. When 50 mg/kg body weight aminoguanidine was injected once daily (n=2 for control and for aminoguanidine-treated rats), the average duration of illness was 5 days for both groups, but the maximum clinical severity was 3.0 for both controls and 1.5 for both aminoguanidine-treated rats. When the same total daily dose of aminoguanidine was administered continuously using subcutaneous Alzet osmotic pumps (Alza Corporation, Palo Alto, Calif.), no beneficial effect of aminoguanidine was observed. This observation suggests that daily injection of aminoguanidine was necessary to inhibit EAE.

Further evidence in support of the inhibition of nitric oxide synthase is provided by the data shown in FIG. 6. Neuronal NADPH diaphorase is now recognized as a NO synthase since both nitric oxide synthase and NADPH diaphorase activities can be immunoprecipitated with an antibody recognizing neuronal NADPH diaphorase (29). Eight rats were paired prior to EAE induction, one receiving aminoguanidine treatment, the other receiving only saline injections. When paralytic disease appeared in the untreated rat, both animals in the pair were killed for histological examination of the CNS and for NADPH diaphorase staining. Histological sections of the spinal cord from these rats were examined for inflammation and the presence and distribution of NADPH diaphorase. Sections from rats with symptomatic EAE and from those treated with aminoguanidine without clinical disease both contained inflammatory infiltrates. In all of these rats, the anterior horn cells were NADPH diaphorase/NO synthase positive (FIG. 6A, 6B); however, only in the spinal cord of clinically ill animals which had not received aminoguanidine were the blood vessel walls strongly positive for this activity (FIG. 6A). The spinal cord parenchymal vessels of aminoguanidine-treated rats stained weakly or were negative for NADPH diaphorase activity (FIG. 6B). This difference was interpreted as an effect of the drug on the expression of NO synthase, and not an aberrancy of staining, because in both groups of rats the anterior horn cells were equally positive, thus indicating a successful enzyme reaction. The likelihood that this blood vessel-associated NO synthase plays an important role in the clinical illness associated with CNS inflammation is supported by evidence that the earliest and most significant inflammation in EAE is vasocentric. Nitric oxide produced by the inducible isoform of NO synthase, acting alone or in concert with other inflammatory mediators, may play a crucial role in disrupting neuroglial physiology leading to EAE-associated paralysis.

The data in this Example 5 demonstrate that aminoguanidine, a selective inhibitor of the inducible isoform of NO synthase, prevents the clinically overt illness associated with T-cell mediated, autoimmune CNS inflammation.

TABLE 1

Effects of aminoguanidine on the clinical and histological parameters of EAE

| Parameter | Controls | Aminoguanidine-Treated |
|---|---|---|
| Duration of illness[a] (days) | 4.7 ± 0.4 (7) | 1.2 ± 1.1[b] (5) |
| Maximum clinical severity[b] (scale from 0 to 3) | 2.2 ± 0.9 (15) | 0.4 ± 0.4[b] (13) |
| Overall illness score[a] (sick days times days at maximum illness) | 11.3 ± 4.5 (7) | 2.4 ± 2.2[b] (5) |
| Average weight loss (% of body weight) | 12.5 ± 5.5 (15) | 8.9 ± 7.5 (13) |
| Histological grade | 2.6 ± 0.7 (8) | 2.3 ± 0.6 (8) |

[a]See FIG. 5 protocol, above, for description of clinical severity scoring.
Significantly different from controls by Students t-test: [b]p <0.001

Four separate tests were performed With n=15 for EAE-induced control rats and n=13 for aminoguanidine-treated EAE rats. In two of these tests, a total of eight control rats were killed at peak illness for histologic assessment of inflammation; paired aminoguanidine-treated rats were killed at the same time. Portions of formalin perfusion-fixed or immersion-fixed rat spinal cords were embedded in paraffin and standard hematoxylin/eosin-stained histological sections were evaluated for the presence of inflammation. Severity of inflammation was graded histologically as: 0, no inflammation; 1, rare, scattered small foci of inflammation; 2, multiple isolated foci; 3, multiple foci with inflammatory confluence; 4, foci of necrosis and/or neutrophilic infiltrate The aminoguanidine inhibitor of nitric oxide formation described herein can be used for administration to warm blooded mammals by conventional means, preferably in formulations with pharmaceutically acceptable diluents and carriers. The amount of the active inhibitor to be administered must be an effective amount, that is, an amount which is medically beneficial but does not present toxic effects which overweigh the advantages which accompany its use. It would be expected that the adult human daily dosage would normally range upward from about one milligram per kilo of body weight of the drug. A suitable route of administration is orally in the form of capsules, tablets, syrups, elixirs and the like, although parenteral administration also can be used, e.g. intraveneously, intraperitoneally or subcutaneously. Intraveneous administration of the drug in aqueous solution such as physiologic saline is illustrative. Appropriate formulations of the drug in pharmaceutically acceptable diluents and carriers in therapeutic dosage form can be prepared by reference to general texts in the field such as, for example, *Remington's Pharmaceutical Sciences*, Ed. Arthur Osol. 16th ed., 1980, Mack Publishing Co., Easton, Pa.

Various other examples will be apparent to the person skilled in the art after reading the present disclosure without departing from the spirit and scope of the invention. It is intended that all such examples be included within the scope of the appended claims.

References cited in parenthesis in the disclosure are appended hereto as follows:

1. D. J. Stuehr, H. J. Cho, N. S. Kwon, M. F. Weise, C. F. Nathan, *Proc. Natl. Acad. Sci. USA* 88, 7773 (1991).
2. S. Moncada, R. M. J. Palmer, E. A. Higgs, *Pharmacol. Reviews* 43, 109 (1991).
3. J. Garthwaite, *Trends Neurol. Sci.* 14:60 (1991).
4. J. B. Hibbs, Jr., et al., in *Nitric Oxide from L-Arginine: a Bioregulatory System*, S. Moncada and E. Higgs, Eds. Elsevier, New York, (1990) pp 189-223.
5. G. Pugliese, R. G. Tilton, J. R. Williamson, *Diabetes/Metabolism Reviews* 7, 35 (1991).
6. C. Southern, D. Schulster, I. C. Green, *Febs Lett.* 276, 42 (1990).
7. J. A. Corbett, J. L. Wang, M. A. Sweetland, J. R. Lancaster, Jr., M. L. McDaniel, *Biochemical J.* (submitted).
8. J. A. Corbett, J. R. Lancester, Jr., M. A. Sweetland, M. L. McDaniel, *J. Biol. Chem.* 266, 21351-21354 (1991).
9. J. R. Williamson et al., *Diabete & Metab.* 16, 3369 (1990). T. Soulis-Liparota, M. Cooper, D. Papazoglou, B. Clarke, G. Jerums, *Diabetes* 40, 1328 (1991).
10. M. Kihara et al., *Proc. Natl. Acad. Sci. USA* 88, 6107 (1991).
11. M. Brownlee, A. Cerami, H. Vlassara, *N. Engl. J. Med.* 318, 1315 (1988). M. Brownlee, H. Vlassara, A. Kooney, P. Ulrich, A. Cerami, *Science* 232, 1629 (1986).
12. R. Bucala, K. J. Tracey, A. Cerami, *J. Clin. Invest.* 87, 432 (1991).
13. Unpublished observations.
14. J. R. Lancaster, Jr., J. B. Hibbs, Jr. *Proc. Natl. Acad. Sci. USA* 87, 1223 (1990).
15. J. C. Drapier, C. Pellat, Y. Henry *J. Biol. Chem.* 266, 10162 (1991).
16. M. A. Beaven, R. E. Shaff *Biochem. Pharmacol.* 24, 979 (1975).
17. J. R. Williamson, *J. Clin. Invest.* 85, 1167 (1990). B. A. Wolf et al., *J. Clin. Invest.* 87, 31 (1991).
18 K. Chang, W. Allison, J. Harlow, J. R. Williamson, *Diabetes* 40, 210A (1991).
19. L. C. Green et al., *Anal. Biochem.* 126, 131 (1982).
20. M. L. McDaniel, J. R. Colca, N. Kotagal, P. E. Lacy, *Methods Enzymol.* 98, 182 (1983).
21. G. Pugliese et al., *Diabetolgia* 32, 847 (1990). G. Pugilese et al., *Metabol* 39, 690 (1990).
22. R. G. Tilton, K. Chang, C. Weigel, C. Kilo, J. R. Williamson, *Invest. Ophthalmal. Vis. Sci.* 29, 861 (1988).
23. R. Arnon, *Immunol. Rev.* 55, 5 (1981); A. Ben-Nun, H. Wekerle, I. R. Cohen, *Eur. J. Immunol.* 11, 195 (1981); A. A. Vandenbark and T. Gill, H. Offner, *J. Immunol.* 135, 223 (1985); H. Lassman et al., *Rev. Neurol.* 147, 763 (1991).
24. W. F. Hickey et al., *J. Immunol.* 131, 2805 (1983); W. F. Hickey, J. A. Cohen, J. B. Burns, *Cell. Immunol.*, 109, 272 (1987); Y. Matsumoto et al., *J. Immunol.* 136, 3668 (1986).
25. S. W. Brostoff and D. W. Mason, *J. Immunol.* 133, 1938 (1984); B. T. Engelhardt, T. Diamanstein, H. Wekerle, *J. Autoimmunity* 2, 61 (1989); G. A. Hashim et al., *J. Immunol.* 144, 4621 (1990).

26. C. F. Brosnan, M. B. Bornstein, B. R. Bloom, *J. Immunol.* 126, 614 (1981).
27. N. Ruddle, *J. Exp. Med.* 172, 1193 (1990); W. J. Karpus and R. H. Swanborg, *J. Neuroimmunol.* 24, 249 (1989); A. Billau et al., *J. Immunol.* 140, 1506 (1988).
28. C. Bolton et al., *J. Neurol. Sci.* 56, 147 (1982); C. F. Brosnan et al., *Proc. Natl. Acad. Sci. U.S.A.* 82, 5915 (1985); A. Komarck and F. M. Dietrich, *Arch. Int. Pharmacodynam. Ther.* 193, 249 (1971); J. M. Lemire and D. C. Archer, *J. Clin. Invest.* 87, 1103 (1991).
29. B. T. Hope et al., *Proc. Natl. Acad. Sci. U.S.A.* 88, 2811 (1991); T. M. Dawson et al., *Proc. Natl. Acad. Sci. U.S.A.* 88, 7797 (1991).

What is claimed is:

1. A method of inhibiting nitric oxide production in a warm blooded mammal afflicted with the physiological conditions manifested by an immunologically-mediated, nitric oxide-mediated disease which comprises administering to said mammal a nitric oxide inhibitory effective amount of aminoguanidine.

2. The method of claim 1 in which the aminoguanidine is administered to the mammal intravenously or subcutaneously.

3. The method of claim 1 in which the aminoguanidine is administered to a mammal at doses which inhibit nitric oxide production without producing a substantial elevation in arterial blood pressure.

4. The method of claim 1 in which the aminoguanidine is administered to a mammal at doses which inhibit nitric oxide synthase in tissues affected by disease processes without inhibiting constitutive vascular nitric oxide synthase that would cause hypertension.

5. The method of claim 1 in which the immunologically-mediated, nitric oxide-mediated disease is multiple sclerosis.

* * * * *